United States Patent
Ahn et al.

(10) Patent No.: US 9,357,754 B2
(45) Date of Patent: Jun. 7, 2016

(54) TRANSGENIC PIG EXPRESSING STNFR1-FC GENES AND THE USES THEREOF

(75) Inventors: Curie Ahn, Gyeonggi-do (KR); Byeong Chun Lee, Seoul (KR); Jong Ik Hwang, Seoul (KR); Jae Seok Yang, Seoul (KR); Byoung Gon Moon, Daejeon (KR); Goo Jang, Seoul (KR); Bum Rae Cho, Seoul (KR); Ok Jae Koo, Seoul (KR); Sol Ji Park, Seoul (KR); Jung Taek Kang, Seoul (KR); Dae Kee Kwon, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 253 days.

(21) Appl. No.: 13/980,846

(22) PCT Filed: Jan. 20, 2012

(86) PCT No.: PCT/KR2012/000578
§ 371 (c)(1),
(2), (4) Date: Oct. 2, 2013

(87) PCT Pub. No.: WO2012/099447
PCT Pub. Date: Jul. 26, 2012

(65) Prior Publication Data
US 2014/0026233 A1    Jan. 23, 2014

(30) Foreign Application Priority Data
Jan. 21, 2011  (KR) .................. 10-2011-0006561

(51) Int. Cl.
| | |
|---|---|
| A01K 67/027 | (2006.01) |
| C12N 15/00 | (2006.01) |
| C12P 21/00 | (2006.01) |
| C07K 14/705 | (2006.01) |
| C12N 15/85 | (2006.01) |
| A61D 19/04 | (2006.01) |
| C07K 16/18 | (2006.01) |
| C07K 14/715 | (2006.01) |
| A61K 38/00 | (2006.01) |

(52) U.S. Cl.
CPC ............ A01K 67/0275 (2013.01); A61D 19/04 (2013.01); C07K 14/70578 (2013.01); C07K 16/18 (2013.01); C12N 15/8509 (2013.01); A01K 2207/15 (2013.01); A01K 2217/052 (2013.01); A01K 2227/108 (2013.01); A01K 2267/025 (2013.01); A61K 38/00 (2013.01); C07K 14/7151 (2013.01); C07K 2319/30 (2013.01)

(58) Field of Classification Search
CPC .................. A61K 49/0008; A61K 2039/505; A61K 39/3955; A61K 47/48546; A61K 39/39558; A61K 38/19; A61K 38/191; C07K 2317/92; C07K 2319/32; C07K 2319/30; C07K 2319/74; A01K 2217/05; A01K 2267/025; A01K 2227/10; A01K 2227/105; A01K 2227/108; A01K 2217/052; A01K 67/0275; A01K 67/0278; A01K 2207/15; A01K 2217/00; C12N 15/8509; C12N 15/62

See application file for complete search history.

(56) References Cited

U.S. PATENT DOCUMENTS

2003/0165480 A1*  9/2003  Zhu .......................... 424/93.21
2005/0268347 A1  12/2005  Tu et al.

FOREIGN PATENT DOCUMENTS

| WO | 96/32478 | 10/1996 |
|---|---|---|
| WO | 97/34631 | 9/1997 |
| WO | 2011081343 A2 | 7/2011 |

OTHER PUBLICATIONS

Sabatine et al. Delayed Rejection of Soluble Tumor Necrosis Factor Receptor-Secreting Tumor Allografts.Transplantation, 1998, vol. 65, pp. 113-120.*

Garcia et al. Transgenic mice expressing high levels of soluble TNF-R1 fusion protein are protected from lethal septic shock and cerebral malaria, and are highly sensitive to Listeria monocytogenes and Leishmania major infections. Eur. J. Immunology, 1995, vol. 25, pp. 2401-2407.*

Fujimara et al. Transgenic mice expressing high levels of soluble TNF-R1 fusion protein are protected from lethal septic shock and cerebral malaria, and are highly sensitive to Listeria monocytogenes and Leishmania major infectionsCloning and Stem Cells, 2004, vol. 6, pp. 294-301.*

Machen et al., "Prolongation of islet allograft survival following ex vivo transduction with adenovirus encoding a soluble type 1 TNF receptor-Ig fusion decor", Gene Therapy, vol. 11, pp. 1506-1514 (Jul. 1, 2004).

(Continued)

*Primary Examiner* — Deborah Crouch
(74) *Attorney, Agent, or Firm* — Joseph R. Baker, Jr.; Gavrilovich, Dodd & Lindsey LLP

(57) ABSTRACT

The present invention relates to a transgenic pig that expresses sTNFR1-Fc, wherein a gene encoding sTNFR1-Fc, which is a fusion protein of the extracellular domain of human soluble tumor necrosis factor receptor (sTNFR1) and an immunoglobulin Fc region, is introduced; a method for preparing the same; an organ isolated from the transgenic pig; a somatic donor cell line inserted with sTNFR1-Fc gene; a method for preparing a blood sample comprising sTNFR1-Fc; and a method for preparing human sTNFR1-Fc from the blood sample of the transgenic pig. As the transgenic pig can suppress immune response and inflammatory response by secreting an inhibitory substance that suppresses the activity of TNF-α in blood, it can be effectively used for xenograft. Furthermore, since the transgenic pig has a blood type O, it can be transplanted for suppressing inflammatory response, regardless of a blood type of recipient.

15 Claims, 5 Drawing Sheets

(56) References Cited

OTHER PUBLICATIONS

Zettlitz et al., "ATROSAB, A humanized antagonistic anti-tumor necrosis factor receptor one-specific antibody", mAbs, vol. 2(6), pp. 639-647 (Nov. 1, 2010).

Vosters et al., "Local expression of tumor necrosis factor-receptor 1: immunoglobulin G can induce salivary gland dystunction in a murine model of Sjoren's syndrome", Arthritis Research & Therapy, vol. 11(6), R189 (Dec. 14, 2009).

Costa et al., "Use of porcine tumor necrosis factor receptor I-Ig fusion protein to prolong xenograft survival", Xenotransplantation, vol. 11, pp. 491-502 (2004).

Rauert et al., "Membrane Tumor Necrosis Factor (TNF) Induces p100 Processing via TNF Receptor-2 (TNFR2)", The Journal of Biological Chemistry, vol. 285(10), pp. 7394-7404 (Mar. 10, 2010).

* cited by examiner

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: forward primer for sTNFR1

<400> SEQUENCE: 1
ataagcttat gggcctctcc accgtgc                                27

<210> SEQ ID NO 2
<211> LENGTH: 22
<212> TYPE: DNA
<213> ORGANISM: Artificial Sequence
<220> FEATURE:
<223> OTHER INFORMATION: reverse primer for sTNFR1

<400> SEQUENCE: 2
tgtggtgcct gagtcctcag tg                                    22

<210> SEQ ID NO 3
<211> LENGTH: 23
<212> TYPE: DNA
<213> ORGANISM: Artificial Sequence
<220> FEATURE:
<223> OTHER INFORMATION: forward primer for human IgG-Fc

<400> SEQUENCE: 3
acatgcccac cgtgcccagc acc                                   23

<210> SEQ ID NO 4
<211> LENGTH: 28
<212> TYPE: DNA
<213> ORGANISM: Artificial Sequence
<220> FEATURE:
<223> OTHER INFORMATION: reverse primer for human IgG-Fc

<400> SEQUENCE: 4
atctcgagtc atttacccgg agacaggg                              28

<210> SEQ ID NO 5
<211> LENGTH: 1305
<212> TYPE: DNA
<213> ORGANISM: Artificial Sequence
<220> FEATURE:
<223> OTHER INFORMATION: Human sTNFR1-Fc

<400> SEQUENCE: 5
atgggcctct ccaccgtgcc tgacctgctg ctgccactgg tgctcctgga gctgttggtg      60
ggaatatacc cctcaggggt tattggactg tccctcacc taggggacag ggagaagaga      120
gatagtgtgt gtccccaagg aaaatatatc caccctcaaa ataattcgat ttgctgtacc     180
aagtgccaca aggaaccta cttgtacaat gactgtccag gcccggggca ggatacggac      240
tgcagggagt gtgagagcgg ctccttcacc gcttcagaaa accacctcag acactgcctc     300
agctgctcca atgccgaaa ggaaatgggt caggtggaga tctcttcttg cacagtggac      360
cgggacaccg tgtgtggctg caggaagaac cagtaccggc attattggag tgaaaacctt      420
ttccagtgct tcaattgcag cctctgcctc aatgggaccg tgcacctctc ctgccaggag     480
aaacagaaca ccgtgtgcac ctgccatgca ggtttctttc taagagaaaa cgagtgtgtc     540
tcctgtagta actgtaagaa aagcctggag tgcacgaagt tgtgcctacc ccagattgag     600

```
aatgttaagg gcactgagga ctcaggcacc acaacatgcc caccgtgccc agcacctgaa      660
ctcctggggg gaccgtcagt cttcctcttc cccccaaaac ccaaggacac cctcatgatc      720
tcccggaccc ctgaggtcac atgcgtggtg gtggacgtga gccacgaaga ccctgaggtc      780
aagttcaact ggtacgtgga cggcgtggag gtgcataatg ccaagacaaa gccgcgggag      840
gagcagtaca acagcacgta ccgtgtggtc agcgtcctca ccgtcctgca ccaggactgg      900
ctgaatggca aggagtacaa gtgcaaggtc tccaacaaag ccctcccagc ccccatcgag      960
aaaaccatct ccaaagccaa agggcagccc cgagaaccac aggtgtacac cctgccccca     1020
tcccgggatg agctgaccaa gaaccaggtc agcctgacct gcctggtcaa aggcttctat     1080
cccagcgaca tcgccgtgga gtgggagagc aatgggcagc cggagaacaa ctacaagacc     1140
acgcctcccg tgctggactc cgacggcccc ttcttcctct acagcaagct caccgtggac     1200
aagagcaggt ggcagcaggg gaacgtcttc tcatgctccg tgatgcatga ggctctgcac     1260
aaccactaca cgcagaagag cctctccctg tctccgggta aatga                      1305
```

TRANSGENIC PIG EXPRESSING STNFR1-FC GENES AND THE USES THEREOF

CROSS REFERENCE TO RELATED APPLICATIONS

This application is a U.S. National Stage Application filed under 35 U.S.C. §371 and claims priority to International Application No. PCT/KR2012/000578, filed Jan. 20, 2012, which application claims priority to Korean Application No. 10-2011-0006561, filed on Jan. 21, 2011, the disclosures of which are incorporated herein by reference.

TECHNICAL FIELD

The present invention relates to a transgenic pig that expresses sTNFR1-Fc, wherein a gene encoding sTNFR1-Fc, which is a fusion protein of the extracellular domain of human soluble tumor necrosis factor receptor (sTNFR1) and an immunoglobulin Fc region, is introduced; a method for preparing the same; an organ isolated from the transgenic pig; a somatic donor cell line inserted with sTNFR1-Fc gene; a method for preparing a blood sample comprising sTNFR1-Fc; and a method for preparing the human sTNFR1-Fc from the blood sample of the transgenic pig.

BACKGROUND

The transformation of an organism is a generic term for multiple techniques including the introduction of a foreign gene into the genome of organism by artificial means and expression of the same; the induction and manipulation of overexpression of intrinsic gene; the knockout of a specific gene on the genome to identify the phenotypic changes induced by the gene expression and the function of the genes, for improving animals and plants, increasing productivity, and for generating useful industrial medical products.

The introduction of a foreign gene into an organism can be done by various methods such as, for the transformant animal, the microinjection to a fertilized egg by microinjector, use of viruses in various forms, use of electromagnetic field, and use of chemicals such as lipids, depending on the purpose. Also, the expression of a target gene can be limited to a specific tissue by using a promoter that can induce the expression of a foreign gene, or can be induced according to the developmental stage of an organism.

Methods of transformation for application to animals have been developed and could be commercialized according to many studies. In particular, transformed and cloned animals have been used for the improvement of livestock and development of new variety, enhancement of disease endurance to the diseases that occur frequently in livestock, improvement of the quality of by-product that can be obtained from livestock, production of disease-model animal, development of organ donor animal that can substitute the organ injury caused by human diseases or natural disasters, and production of useful substance using a bioreactor system.

Cloning refers to the generation of a genetically identical subject. Nuclear transfer is one of the cloning methods for eukaryotes and it grabs new attention due to recent developments in molecular biology field. Early nuclear transfer technique used a blastomere of fertilized egg as nuclear donor (Prather et al., Biol. Reprod., 1987, 37:856-866; Prather et al., Biol. Reprod., 1989, 41:414-418), but recently a nucleus of somatic cell is used instead.

Somatic cell cloning is a technique for creating a fertilized egg by inserting a differentiated somatic cell to enucleated oocyte and activating the same. Said cloning technique not only can be widely used in the researches in basic science field including developmental biology, but is also expected to provide large contribution to various medical and pharmacological fields such as production of useful proteins, development of disease-model, and organ transfer, thereby demonstrating a large industrial usefulness. That is, a production system using said technique is highly cost-effective, and thus it can produce a bioactive substance at lower cost, which is currently sold at a high price. Furthermore, said production system utilizes the animal that is physiologically closest to a human body as a system for producing physiologically active substance, and thus high quality product can be produced. Also, since the in vivo protein production system of animal is used, a large-scale production is possible, and particularly for drug development such as vaccine for ingestion, no separate purification process is needed.

Meanwhile, as for organ transplantation, which transplants a portion of or whole organ to a recipient who lost a functional organ and thus cannot receive any more treatment such as drug treatment, those organs are mostly taken from live persons. However, the number of donors is significantly lower than the number of waiting recipients. Thus, there have been many attempts to solve these problems. For instance, stem cell transplantation and transplantation of xenogeneic organ have been developed. The stem cell transplantation can be used to substitute damaged cells by proliferating the cells as many as required, but these cells cannot be developed into an organ, which is composed of various types of cells. Thus, if organ transplantation is needed, xenograft may be used to directly replace the damaged organ. Heteroplastic transplantation using animals, which can provide sufficient number of donor organs, has been emerged as one of various methods that can substitute human organ. However, when a xenogeneic organ is transplanted to human body, severe multiphasic immune responses and inflammatory responses are induced. In particular, pigs have very similar anatomical and physiological structure as humans, and the organ size thereof is similar to that of humans. Also, transplantation of pig organ has advantages of easy breeding, short pregnancy period (112 days), and bearing a large number of piglings at once (6 to 12). However, when the pig organ is transplanted in human body, severe multiphasic immune responses and inflammatory responses will be induced. Therefore, resolving the problem of immune response and inflammatory response is a remaining task to be solved for conducting heteroplastic transplantation.

DISCLOSURE

Technical Problem

In an effort for developing a method of suppressing immunorejection upon heteroplastic transplantation and inflammatory response after transplantation, the present inventors have prepared a cloned transgenic pig, wherein a gene encoding TNFR1-Fc fusion protein, which is a fusion protein of the extracellular domain of human TNFR1 and an IgG Fc region, is introduced, and confirmed the expression and secretion of TNFR1-Fc in the tissue and blood of the transgenic pig and the reduction in chemokine expression induced by TNF-α, which is an inflammatory cytokine, thereby completing the present invention.

Technical Solution

One object of the present invention is to provide a transgenic pig that expresses sTNFR1-Fc, wherein a gene encoding sTNFR1-Fc, which is a fusion protein of the extracellular domain of human soluble tumor necrosis factor receptor (sTNFR1) and an immunoglobulin Fc region, is introduced.

Another object of the present invention is to provide a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced.

Another object of the present invention is to provide a method for preparing the transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced, comprising (a) introducing a gene encoding human sTNFR1-Fc into the somatic cells isolated from a pig; (b) preparing an embryo transferred with the nucleus of somatic cell by fusing the gene-introduced somatic cells with an enucleated porcine oocyte; and (c) implanting the embryo.

Another object of the present invention is to provide an organ isolated from the transgenic pig.

Another object of the present invention is to provide a somatic donor cell line inserted with a gene encoding sTNFR1-Fc, which is a fusion protein of the extracellular domain of human sTNFR1 and an immunoglobulin Fc region.

Another object of the present invention is to provide a method for preparing a blood sample, comprising preparing a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced; and isolating the blood sample.

Another object of the present invention is to provide a method for preparing human sTNFR1-Fc, comprising preparing a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced; and isolating human sTNFR1-Fc from the blood of the transgenic pig.

Advantageous Effects

The transgenic pig prepared in the present invention expresses and secretes TNFR1-Fc in the tissue or blood, and thereby can suppress the TNF-α-mediated inflammatory response, which occurs at the early phase of transplantation and also can reduce the immunorejection by suppressing the maturation of dendritic cells and by regulating the proliferation and activation of T cells. Therefore, the present transgenic pig can be effectively used for heteroplastic transplantation. Also, the transgenic pig of the present invention has a blood type of O, and thus the blood sample thereof can be isolated and transplanted to a subject in need of the suppression of inflammatory response, regardless of the blood type of a recipient.

BEST MODE

Figure 1:
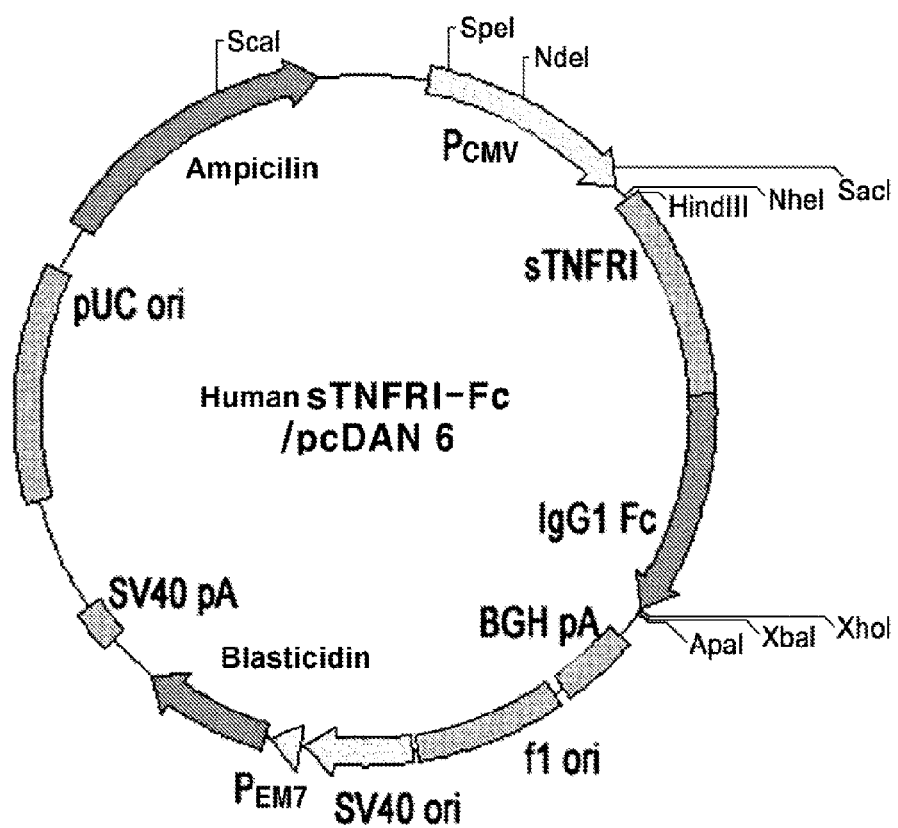
FIG. 1 shows a schematic diagram of the sTNFR1-Fc expression vector.

As one aspect to achieve the above objectives, the present invention provides a transgenic pig that expresses sTNFR1-Fc, wherein a gene encoding sTNFR1-Fc, which is a fusion protein of the extracellular domain of human soluble tumor necrosis factor receptor (sTNFR1) and an immunoglobulin Fc region, is introduced.

To be more specific, the present invention provides a transgenic pig that secretes sTNFR1-Fc into blood, wherein a gene encoding sTNFR1-Fc, which is a fusion protein of the extracellular domain of human sTNFR1 and an immunoglobulin Fc region, is introduced.

As used herein, the term "gene encoding tumor necrosis factor receptor 1-Fc (TNFR1-Fc)" refers to a gene encoding a fusion protein of the extracellular domain of TNFR1 and the immunoglobulin Fc region, that can bind to TNF-α. As used herein, the terms "gene encoding TNFR1-Fc" and "TNFR1-Fc fusion gene," or "TNFR1-Fc gene" can be used interchangeably.

As used herein, the term "TNF-α" is a cytokine that is mainly produced by activated monocytes and macrophages and is a strong proinflammatory mediator.

In the present invention, any form of TNFR1-Fc may be used without limitation, as long as it can bind to TNF-α and inhibit the same. Preferably, a soluble form like soluble TNFR1 (sTNFR1) and a fused form of TNFR1 with immunoglobulin Fc region may be used. As used herein, the term "immunoglobulin Fc region" refers to the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin, and it may comprise a hinge region of heavy-chain constant region. Also, the immunoglobulin Fc region of the present invention may be the extended Fc region comprising a partial or whole of the heavy-chain constant region 1 (CH1) and/or the light-chain constant region 1 (CL1), excluding the heavy chain and light chain variable regions of immunoglobulin, as long as it has substantially the same or improved effect than the native protein. In addition, the Ig Fc region may be the fragment wherein a significantly long portion of the amino acid sequence corresponding to CH2 and/or CH3 is deleted. That is, the immunoglobulin Fc region of the present invention may be 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more than two domains and an immunoglobulin hinge region (or a portion of the hinge region), and 6) a dimer of each domain of the heavy-chain constant regions and the light-chain constant region. Furthermore, the immunoglobulin Fc region of the present invention may be not only a native amino acid sequence, but also a sequence derivative thereof. An amino acid sequence derivative refers to the sequence that is different from a native amino acid sequence due to a deletion, insertion, non-conservative or conservative substitution of one or more amino acid residues, or a combination thereof. For example, as for the IgG Fc, the amino acid residues at the position of 214 to 238, 297 to 299, 318 to 322, or 327 to 331, which are known to be important for binding, may be used as a suitable target for protein modification. Also, other types of derivatives may be formed by deletion of a region capable of forming a disulfide bond, deletion of few amino acids at the N-terminal of native Fc, or addition of methionine residue at the N-terminal of native Fc. In addition, a complement-binding site, e.g., C1q-binding site or ADCC site may be deleted in order to remove the effector function. The methods for generating said sequence derivatives of the immunoglobulin Fc region are disclosed in International Patent Publication Nos: WO 97/34631 and WO 96/32478 Amino acid exchange in proteins and peptides, which does not change the molecular activity as a whole, is known in the art. The most commonly-occurring amino acid exchanges are between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly. Depending on the case, the Fc region may be modified by phosphorylation, sulfation, acrylation, glycosylation, methylation, farnesylation, acetylation, amidation, and the like. The aforementioned Fc derivatives demonstrate the same biological activity as the Fc region of the present invention, but with the improved constitutional stability against heat and pH changes.

Meanwhile, the immunoglobulin Fc region may be derived from humans or other animals including cows, goats, swine, mice, rabbits, hamsters, rats and guinea pigs, and preferably humans. In addition, the immunoglobulin Fc region may be the Fc regions derived from IgG, IgA, IgD, IgE and IgM, or a combination or hybrid thereof. Preferably, it is derived from IgG or IgM, which is the most abundant protein in human blood, and most preferably from IgG, which is known to enhance the half-life of a ligand-binding protein.

As used herein, the term "combination" means that when forming a dimer or multimer, a polypeptide encoding single-chain immunoglobulin Fc regions of the same origin is linked to a single-chain polypeptide of a different origin. That is, a dimer or multimer may be formed from two or more fragments selected from the group consisting of IgG Fc, IgA Fc, IgM Fc, IgD Fc, and IgE Fc fragments.

As used herein, the term "hybrid" means that sequences encoding two or more immunoglobulin Fc regions of different origin are present in a single-chain immunoglobulin Fc region. In the present invention, various types of hybrids may be used. That is, a hybrid of domains may comprise one to four domains selected from the group consisting of CH1, CH2, CH3 and CH4 of IgG Fc, IgM Fc, IgA Fc, IgE Fc and IgD Fc, and may comprise a hinge region. On the other hand, IgG can also be divided into IgG1, IgG2, IgG3 and IgG4 subclasses, and the present invention includes a combination or hybrid thereof.

As used herein, a fusion protein of a receptor of TNF-α and an immunoglobulin has the following advantages over a monomer of the intrinsic molecule or a molecule not combined with Ig:

(1) the fusion protein has increased total avidity to a ligand because it has bivalency in a dimer form;
(2) the fusion protein is present in an undestroyed form in serum for a longer period of time by virtue of increased molecular stability;
(3) effector cells are activated by the fragment crystallizable (Fc) region of the immunoglobulin heavy chain; and
(4) the fusion protein is isolated and purified by a convenient method (e.g., isolation and purification using protein A).

The fusion protein of the present invention is generated in a form excluding a CH1 domain of heavy chain, and as a result, it may be formed as a dimer which does not bind to the light chain of immunoglobulin.

The sequence of the gene encoding each of human TNFR1 protein and Fc may be obtained from the known database. Any sequence may be used without limitation, as long as it shows the function of TNFR1-Fc fusion protein, when inserted into a porcine somatic cell, and preferably the gene encoding TNFR1-Fc fusion protein represented by SEQ ID NO: 5 may be used.

As used herein, the term "transgenic pig" means a pig that is genetically modified by artificial insertion of a foreign piece of gene into the porcine genome.

The transgenic pig of the present invention is characterized in that the inserted gene encoding sTNFR1-Fc and sTNFR1-Fc proteins are expressed and secreted not only in the tissues of transgenic pig, but also in blood, thereby suppressing the activity of TNF-α, which is a cytokine acting as a strong proinflammatory mediator.

The tissues of the present invention include a heart, stomach, small intestine, large intestine, kidney, liver, lung, and pancreas without limitation, and preferably pancreas or islet cells isolated from pancreas.

The transgenic pig of the present invention expresses sTNFR1-Fc not only in the tissues thereof but also in blood, and has the advantage of expressing the protein in the form of a secretory protein. Also, as the sTNFR1-Fc is expressed in a form of secretory protein in blood, the sTNFR1-Fc can be easily isolated from the blood without sacrificing a transgenic pig and used for preparing a composition for suppressing inflammatory mediator such as TNF-α. Said transgenic pig that secretes sTNFR1-Fc into blood was developed by the present inventors for the first time.

Figure 7:
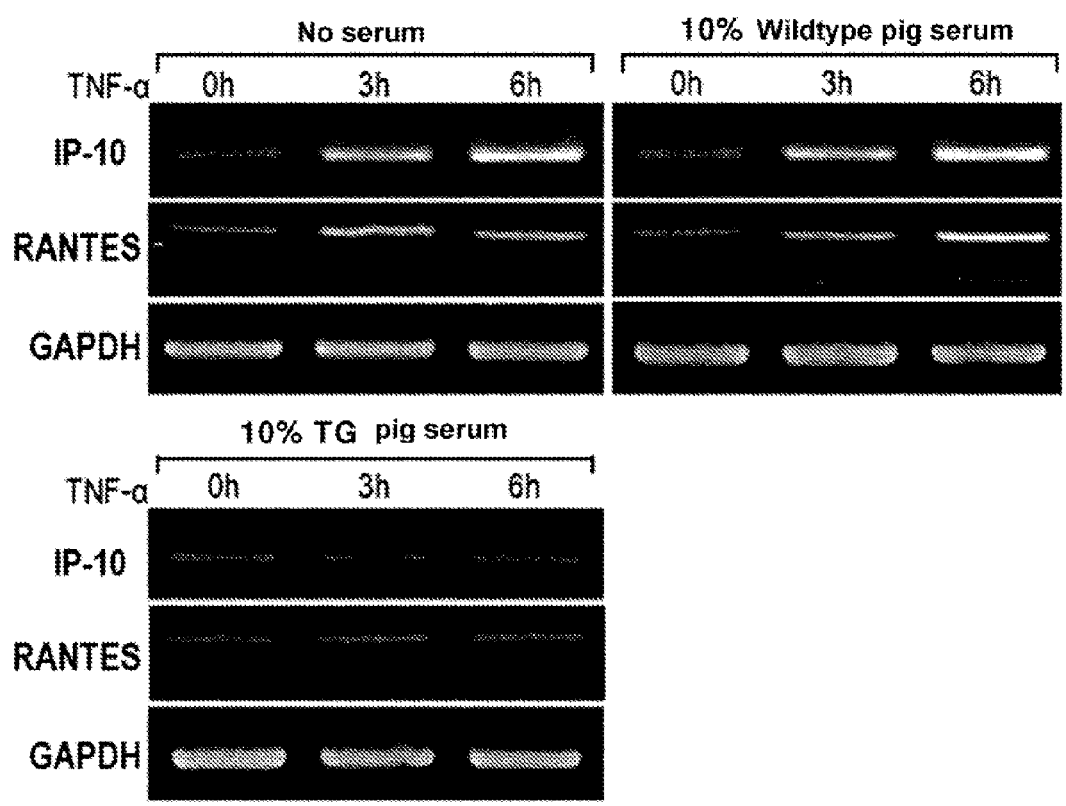
FIG. 7 shows analysis of the activation level of vascular endothelial cell line after adding human TNF-α to each of the test groups with no serum added, the test group added with wild-type serum, and the test group added with the serum of the transgenic pig of the present invention. It was observed that the expression of IP-10 and RANTES was suppressed in the transgenic pig of the present invention, compared to other test groups.

In one example of the present invention, the expression of sTNFR1-Fc gene in a tail tissue and peripheral blood monocyte of transgenic pig was confirmed by PCR and RT-PCR, and the expression of sTNFR1-Fc protein was also confirmed by Western blotting and immunostaining using the ear and tail tissues of transgenic pig, thereby confirming that sTNFR1-Fc can be expressed in every tissue of the pig (Example 8). In addition, as a result of analyzing the activation level of vascular endothelial cell line (MPN3) of transgenic pig after treating the same with TNF-α, it was observed that the expression of chemokine such as IP-10 and RANTES was suppressed in the blood of transgenic pig prepared in the present invention, in comparison to a native pig (FIG. 7). This suggests that the transgenic pig of the present invention can suppress not only the immunorejection caused by xenograft but also the inflammatory response and that it can secrete a TNF-α inhibitor. Therefore, the transgenic pig of the present invention may be used as sTNFR1-Fc-secreting pig that can suppress inflammatory response and also as organ donors for xenotranplantation that does not cause inflammatory response and immunorejection. In addition, the transgenic pig of the present invention has a blood type O, and thus the blood isolated from the pig can be transplanted into a subject that needs suppression of inflammatory response, regardless of the blood type of recipient.

As another aspect, the present invention provides a method for preparing a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced, comprising (a) introducing a gene encoding human sTNFR1-Fc into the somatic cells isolated from a pig; (b) preparing an embryo transferred with the nucleus of somatic cell by fusing the gene-introduced somatic cells with an enucleated porcine oocyte; and (c) implanting the embryo.

The somatic cells isolated from the pig in step (a) may be fetal or adult somatic cells of a pig without any limitation. If a fetus of pig is used, it is preferably at day 20 to 40 of gestation, and more preferably at day 25 to 35 of gestation. In addition, the nuclear donor cell is preferably obtained from a fetus of a pig having a blood type O. In one specific example of the present invention, the porcine somatic cells were isolated from a fetus of pig at day 25 to 35 of gestation and having a blood type O. For isolation of the somatic cells, any known method may be used without limitation. In one specific example of the present invention, the skin on the back of the porcine fetus was isolated using a scalpel blade to obtain fibroblasts.

In step (a) of introducing a gene encoding human sTNFR1-Fc into the somatic cells, the gene encoding human TNFR1-Fc may preferably be a gene represented by SEQ ID No. 5.

The somatic cells inserted with the gene encoding human sTNFR1-Fc in step (b) may be prepared by introducing an expression vector comprising the gene.

As a method of transfecting the gene into the cells, a biochemical method, physical method, or a virus-mediated transfection method may be used. Preferably, as a biochemical method, FuGene6 (Roche, USA), Lipofectamine™ 2000 (Invitrogen, USA), or ExGen 500 (MBI Fermentas International Inc., Canada) may be used, and more preferably a lipid-mediated transfection using Lipofectamine may be used. In addition, the expression vector comprising the gene may be any type of expression vector that can be expressed in porcine somatic cell lines.

As used herein, the term "vector" refers to an expression vector capable of expressing a target gene in the cells inserted with the vector, and a gene construct comprising essential regulatory elements, wherein a gene insert is operably linked to be expressed. Preferably, a recombinant vector comprising a gene encoding human TNFR1-Fc may be prepared in the present invention, and by introducing the prepared recombinant vector into the somatic cells, a donor cell line for preparing transgenic embryos can be prepared.

Preferably, the promoter used in the present invention may be any type of promoter that is commonly used in the art for the production of expression vectors, without any limitation. Examples of such promoter include a CMV promoter, a SV40 promoter, and a CAG promoter, but the promoter sequences that can be used in the present invention are not limited thereto. A specific type of promoter may be used for tissue-specific expression of gene, if necessary. In addition, the polyadenylation sequence of the present invention may preferably be a commonly-used polyadenylation sequence, for example, an SV40 polyadenylation sequence, a human growth hormone polyadenylation sequence, a mouse protamine-1 gene polyadenylation sequence (protamine-1 polyA signal), a large T antigen polyA region-derived polyadenylation sequence, a rabbit β-globin-derived polyadenylation sequence, or fetal bovine growth hormone polyadenylation sequence, without any limitation.

In order to confirm the expression of the gene encoding human TNFR1-Fc fusion protein, the vector of the present invention may further comprise a tag sequence for purification or identification of protein. Examples of said tag sequence include GFP, glutathione S-transferase (GST)-tag, HA, His-tag, Myc-tag, and T7-tag, but the tag sequence of the present invention is not limited thereto.

In one specific example of the present invention, as an expression vector comprising the gene encoding human TNFR1-Fc, a pcDNA6 plasmid was used, and said plasmid is prepared by inserting a gene encoding sTNFRI-Fc fusion protein at the HindIII and XhoI restriction enzyme recognition sites of the protein expression vector, wherein the expression is regulated by CMV promoter.

The somatic cells introduced with the expression vector can be easily selected by using an expression vector introduced with a selection marker. An antibiotic resistance gene may be used as a selection marker. The antibiotic resistance gene may be $bsd^r$, $neo^r$, $pac^r$, $bsr^r$, or $hph^r$, but is not limited thereto.

The oocyte used in step (b) may be obtained by culturing the immature oocytes collected from an ovary of gilts.

As used herein, the term "nuclear transfer" refers to the transferring of the nucleus of a cell into an enucleated oocyte, and a subject born by such implantation of the nuclear transferred embryo is a genetically completely identical clone, since the genetic material of a nuclear donor cell is transferred to the cytoplast of a recipient.

As a method for removing the genetic materials of the oocytes, physical removal, chemical treatment, and centrifugation with Cytochalasin B treatment may be used (Tatham et al., Hum Reprod., 11(7); 1499-1503, 1996). In the present invention, the physical enucleation method using a micromanipulator was used. A gene-targeted somatic cell is introduced into an enucleated oocyte by using a technique such as cell fusion method and intracytoplasmic microinjection. The cell fusion method is simple and suitable for a large-scale production of embryos. The intracytoplasmic microinjection maximizes the contact between a nucleus and the intracellular materials in oocyte. The fusion of somatic cell and enucleated oocyte is done by changing the viscosity of cell membrane through electric stimulation. Here, an electric cell manipulator that can easily control micro-current and voltage will be useful for this method. In one specific example of the present invention, the nucleus of the oocyte was physically removed by micromanipulation, and the enucleated oocyte was fused to the above-selected somatic donor cell line by electric stimulation, thereby generating an embryo.

In step (c), the surrogate mother pig for implantation of an embryo transferred with the somatic cell nucleus is preferably a subject in estrus. The nucleus-transferred embryos are activated and grown to the stage where they can be implanted, and then implanted to a surrogate mother. Activation of cloned embryo refers to the reinitiation of cell cycle, which was temporarily quiescent during the maturing process to allow cell division of embryo. To activate the cloned embryo, activities of cell cycle arrest factors, including cell signalling molecules such as MPF and MAP kinase, have to be inhibited, and for this inhibition, it is essential to increase the intracellular level of calcium ions in a cloned embryo. For this, either a calcium influx is drastically increased by changing the cell membrane permeability through a strong electric stimulation or the activities of cell cycle arrest factors are suppressed directly by chemical treatment with ionomycin and 6-DMAP, or both methods can be used concurrently.

As another aspect, the present invention provides an organ isolated from a transgenic pig that expresses sTNFR1-Fc, wherein a gene encoding sTNFR1-Fc, which is a fusion protein of the extracellular domain of human soluble tumor necrosis factor receptor (sTNFR1) and an immunoglobulin Fc region, is introduced.

The organ may refer to not only an organ itself, but also the one comprising blood, and the organ is preferably an organ comprising the blood wherein sTNFR1-Fc, which is a fusion protein of the extracellular domain of human soluble tumor necrosis factor receptor (sTNFR1) and immunoglobulin Fc region, is secreted.

The organ may be a heart, stomach, small intestine, large intestine, kidney, liver, lung, or pancreas without limitation, and preferably it may be pancreas or islet cells isolated from pancreas.

The organ may have the alleviated inflammatory response caused by immunorejection upon transplantation, compared to other organ isolated from a pig that does not secrete soluble tumor necrosis factor receptor 1-Fc (sTNFR1-Fc) into blood.

The organ isolated from the transgenic pig of the present invention expresses sTNFR1-Fc in organ, and secretes the same into blood, and thus when the organ is transplanted into the same or different species, it can suppress immunorejection and inflammatory response by inhibiting the activity of TNF-α present in the blood of recipient. Therefore, the organ of the present invention may be transplanted to a subject in need of organ transplantation, and can treat the disease according to the target organ. A subject in need of the organ transplantation may be an animal or human.

As another aspect, the present invention provides a somatic donor cell line inserted with a gene encoding sTNFR1-Fc, which is a fusion protein of the extracellular domain of human soluble tumor necrosis factor receptor (sTNFR1) and an immunoglobulin Fc region.

The somatic donor cell line is preferably a primary fibroblast cell line isolated from a pig having a blood type O.

The somatic donor cell line may be any type of cell line that can stably express a human TNFR1-Fc fusion gene, without limitation, and preferably it may be the somatic donor cell line identified by Accession No: KCLRF-BP-00249.

According to the method of the present invention, the gene encoding human TNFR1-Fc was efficiently inserted into porcine somatic cells, and then the porcine somatic donor cell line expressing the gene encoding human TNFR1-Fc fusion protein was selected. The somatic donor cell line is characterized in that the expression vector is inserted at the same position in the genome. If the gene is not introduced through the expression vector to a somatic donor cell line, although the gene can still be introduced by itself, the insertion site of the gene will be different among different somatic cells. Protein expression pattern may differ for each cell depending on where the gene is inserted in the chromosome. Therefore, if these cells are used to prepare transgenic pigs, then the phenotype of gene introduced into each subject will be slightly different. In one specific example of the present invention, the somatic donor cell line was established to solve the problem, and it was deposited at the Korean Cell Line Bank (7th floor, Cancer Research Institute, school of medicine, Seoul National University, 28, Yeongeon-dong, Jongno-gu, Seoul) with Accession No. KCLRF-BP-00249 on Dec. 21, 2010.

As another aspect, the present invention provides a method for preparing a blood sample, comprising preparing a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced; and isolating the blood sample.

The blood sample is the blood, wherein sTNFR1-Fc is secreted, and can be used for alleviating immunorejection and inflammatory response. Also, the blood sample can be used in a composition for the prevention or treatment of inflammatory diseases.

Proinflammatory cytokines such as tumor necrosis factor-α (TNF-α) and interleukin-1 (IL-1) are known as a biological substance taking an important role in immune response and inflammatory response. Proinflammatory cytokines are produced by different types of cells such as monocyte or macrophage in response to infection and other cellular stress. When present in a suitable amount, these cytokines take important roles in immune response or inflammatory response, but when they are overproduced, this will lead to the development of various inflammatory diseases. In particular, the overexpression or unregulated production of TNF-α has been a cause of the onset of diseases such as rheumatic arthritis, rheumatic spondylitis, osteoarthritis, and arthritis.

In one specific example of the present invention, the expression of gene encoding sTNFR1-Fc was confirmed in a tail, ear tissue and peripheral blood monocyte of transgenic pig. Also, it was observed that when serum was treated with TNF-α, the expression of chemokines such as IP-10 and RANTES was inhibited, thereby confirming the secretion of inhibitory substance of TNF-α.

Based on the above, it is evident that the blood sample isolated from the transgenic pig of the present invention can be used for the prevention or treatment of inflammatory diseases. The inflammatory diseases include rheumatic arthritis, rheumatic spondylitis, osteoarthritis, and arthritis; sepsis, septic shock, endotoxin shock, gram-negative sepsis, toxic shock syndrome, adult respiratory distress syndrome, malaria cerevra, chronic lung inflammatory disease, silicosis, pulmonary sarcosis, bone resorption, reperfusion injury, graft versus host reaction, allograft rejection, myalgia and febricity caused by infection, for example, secondary cachexia caused by influenza infection, secondary cachexia caused by acquired immune deficiency syndrome (AIDS), AIDS, complications associated with AIDS, keloid formation, scar tissue formation, Crohn's disease, ulcerative colitis, paralysis, non-insulin-dependent diabetes mellitus, multiple sclerosis, inflammatory bowel disease, and viral infection, for example, HIV, influenza virus, and herpes virus including herpes simplex virus type 1 (HSV-1), herpes simplex virus type 2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies, and rhinotracheitis.

The composition of the present invention may be administered to a subject through any method known to persons skilled in the art. The composition may be administered through any administration route, to be specific, intraperitoneal or intrapleural administration, subcutaneous administration, intravenous or intraarterial administration, intramuscular administration, or local injection. Also, the composition of the present invention may be co-administered with other substances that can suppress inflammatory response.

The composition may be sterilized or comprise a preservative, stabilizer, wettable powder, or oil catalyst, a salt for regulating osmotic pressure, or an adjuvant such as buffer, and other therapeutically effective substances. Furthermore, the composition may be prepared by a conventional mixing, granulation, or coating method.

The composition for cytotherapy according to the present invention may comprise a pharmaceutically acceptable carrier or excipient. In addition to active ingredients, the composition may comprise a diluent (e.g., dextrose, sorbitol, cellulose, glycine, lactose, sucrose, mannitol), a binding agent (e.g., magnesium aluminum silicate, starch paste, tragacanth, sodium carboxymethyl cellulose), a disintegrating agent (e.g., starch, agar, alginic acid, or sodium salt thereof) or similar mixture, and/or an absorbent, a colorant, a flavoring agent, and a sweetening agent.

As another aspect, the present invention provides a method for preparing human sTNFR1-Fc, comprising preparing a transgenic pig that secretes sTNFR1-Fc into blood, wherein a gene encoding sTNFR1-Fc, which is a fusion protein of the extracellular domain of human soluble tumor necrosis factor receptor (sTNFR1) and an immunoglobulin Fc region, is introduced; and isolating human sTNFR1-Fc from the blood of the transgenic pig.

A somatic donor cell line of the disclosure was deposited on Dec. 21, 2010 with the Korean Cell Line Bank (7th Floor, Cancer Research institute, School of Medicine, Seoul National University, 28, Yeongeon-dong, Jongno-gu, Seoul), as Accession Number KCLRF-BP-00249 under the Budapest Treaty. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

MODE FOR INVENTION

Hereinafter, the present invention is described in more detail with reference to Examples. However, these Examples are for illustrative purposes only, and the scope of the invention is not intended to be limited by these Examples.

Example 1

Construction of the sTNFR1-Fc Fusion Gene-Expressing Vector

The sequence of the gene encoding a tumor necrosis factor receptor 1 (TNFR1) was analyzed by using NCBI website (http://www.ncbi.nlm.nih.gov/) and ExPASy website (http://expasy.org/) and based on this sequence, the forward primer (5'-ataagcttat gggcctctccaccgtgc-3', SEQ ID NO: 1) and the reverse primer (5'-tgtggtgcct gagtcctcagtg-3', SEQ ID NO: 2) of the extracellular domain of TNFR1 were prepared. Also, through the sequence analysis of a human immunoglobulin G1 gene, the forward primer (5'-acatgccaccgtgcccagc acc-3', SEQ ID NO: 3) and reverse primer (5'-atctcgagtcatttacccg-gagacaggg-3', SEQ ID NO: 4) of Fc region were prepared. Using the prepared primers, a soluble TNFR1 and immunoglobulin G1-Fc (IgG1-Fc) fusion gene were obtained by PCR (sTNFR1-Fc, SEQ ID NO: 5). In order to express the obtained gene, an expression vector pcDNA6 (Invitrogen, CA, USA), which comprises a blasticidine resistance gene and whose expression is controlled via CMV promoter, was digested with HindIII and XhoI restriction enzymes, and the obtained sTNFR1 gene and IgG1-Fc fusion gene were inserted into the restriction sites so as to construct a sTNFR1-Fc gene-expressing vector. A detailed schematic diagram of the expression vector is shown in FIG. 1.

The cells expressing sTNFRI-Fc fusion protein via CMV promoter could be selected by treating the cells with blasticidine.

Example 2

Isolation and Culturing of Nuclear Donor Cell

Fibroblasts obtained from fetal pigs having a blood type O were used as a nuclear donor cell. Firstly, fetal pigs were obtained from sows between day 25 to 35 of gestation by cesarean. The skin on the back of the fetal pig was removed using a scalpel blade, and washed with Dulbecco's Phosphate Buffered Saline (DPBS) three times, and then minced. The minced skin tissues were treated with Dulbecco's modified Eagle's medium (DMEM; Gibco Life Technologies, MD, USA) containing 0.25% trypsin and 1 mM EDTA at 37° C. for 1 hour. The trypsin-treated cells were washed with $Ca^{2+}$- and $Mg^{2+}$-free DPBS once, and centrifuged at 300×g for 2 minutes, and then inoculated in a 60 mm plastic culture dish (Becton Dickinson, NJ, USA). Subsequently, the cells were cultured in DMEM containing 10% (v/v) FBS, 1 mM glutamine, 25 mM $NaHCO_3$, and 1% (v/v) minimum essential medium (MEM) non-essential amino acid solution (Invitrogen, CA, USA) at 39° C. and in 5% $CO_2$ and 95% air for 3 to 4 days. The cells were cultured until saturation point. Then the cells unattached to the culture dish were removed first, and the attached cells were detached from the culture dish by treating them with a medium containing 0.1% trypsin and 0.02% EDTA for 1 minute, and transferred to three new culture dishes for subculture at 4 to 6 intervals.

For cryopreservation, the cells were detached from the culture dish by treating them with a medium containing 0.1% trypsin and 0.02% EDTA for 1 minute, and then put in a freezing medium consisting of 80% (v/v) DMEM, 10% (v/v) DMSO, and 10% (v/v) FBS, and aliquoted into cryotubes, followed by storing at −196° C. in liquid nitrogen.

Example 3

Preparation of Somatic Donor Cell Line

Figure 2:
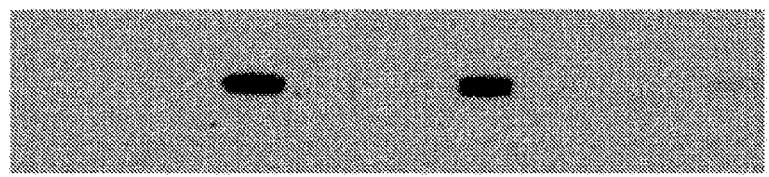
FIG. 2 shows the results of Western blotting to confirm the expression of sTNFR1-Fc in the somatic donor cell line.

Porcine fibroblasts were seeded in a 35 mm plastic culture dish (Becton Dickinson, NJ, USA) at a density of $3 \times 10^5$ cells/well, and the next morning, 1 ug of the gene expression vector (pcDNA6/sTNFR1-Fc), which was prepared in Example 1 and linearized by the restriction enzyme ScaI, was diluted with 50 ul of Opti-MEM I Reduced Serum Medium (Invitrogen, CA, USA). Also, Lipofectamine™2000 having a same volume as the gene expression vector was diluted in 50 ul of Opti-MEM I medium, and incubated at a room temperature for 5 minutes. After incubation, the diluted sTNFR1-Fc expression vector and the diluted Lipofectamine™2000 were mixed together and incubated at a room temperature for 20 minutes. After incubation, the mixture was added to the cells in a 35 mm culture dish, and cultured at 37° C. in $CO_2$ incubator. After 4 hours, the media was replaced with DMEM (Invitrogen, CA, USA) supplemented with 10% FBS and penicillin/streptomycin, and then cultured at 37° C. in a $CO_2$ incubator. After 2 days, the cells were treated with trypsin (Sigma, MO, USA), and transferred to a 100 mm culture dish (Becton Dickinson, NJ, USA). Then after 2 days, the medium was replaced with fresh DMEM (10% FBS, penicillin/streptomycin) containing 5 ug/ml blasticidine (Sigma, MO, USA) every two days during 1 week of cell culturing. Then the cells were cultured in a medium containing 1 ug/ml blasticidine. When the colonies are observed with the naked eyes, 50 or more colonies were selected by using yellow tips, and transferred to a 48-well plate (Becton Dickinson, NJ, USA). According to the cell growth conditions, each colony was transferred to a 12-well plate, a 6-well plate, and a 60 mm culture dish. When the cells were transferred to a 6-well plate, a small amount of cells were taken and the proteins were extracted therefrom. Then, the isolated proteins were run through SDS-PAGE and the expression of sTNFR1-Fc protein was examined by western blotting using anti-human IgG antibody (Santa Cruz Biotechnology, CA, USA) (FIG. 2).

To perform western blotting, the cell lysate was subjected to electrophoresis, and then transferred to a PVDF membrane. Then, the PVDF membrane was blocked with a blocking buffer (5% skim milk in TBST) for 1 hour. After blocking, the membrane was reacted with HRP-conjugated anti-human IgG antibody (Santa Cruz Biotechnology, CA, USA), which was diluted at a ratio of 1:5000, and incubated at a room temperature for 1 hour. After the reaction, the membrane was washed with TBST buffer three times, treated with chemiluminescent substrate (WestSaveUp™, Abfrontier, Seoul, Korea), and then exposed to X-ray film to get the image.

As a result, the cells that were confirmed to have protein expression were transferred to a 100 mm culture dish and cultured for cell proliferation. The cultured cells were aliquoted to 10 cryovials for cryopreservation. The established cell line was named as sTNFRI-Fc line 1 (002-091026), and deposited at Korean Cell Line Bank with Accession No. KCLRF-BP-00249 on Dec. 21, 2010.

Example 4

Collection of Immature Porcine Oocyte and Ex Vivo Maturation

Ovaries were collected from gilts at a slaughterhouse and transported to the laboratory in 0.9% saline solution at 30 to 35° C. Immature oocytes with follicular fluid and cumulus cells were aspirated and collected from 2 to 6 mm follicles using an 18 gauge needle attached to a 10 ml syringe. The aspirated follicular fluid was held at 37° C. in water bath, and only the precipitates were put in the 0.1% polyvinyl alcohol (PVA)-added TLHEPES-PVA (114 mM NaCl, 3.2 mM KCl, 2 mM $NaHCO_3$, 0.4 mM $NaH_2PO_4$, 0.27 mM glucose, 10 mM sodium lactate, 2 mM $CaCl_2$ $2H_2O$, 0.5 mM $MgCl_2 6H_2O$, 10 mM HEPES, 0.03 mM phenol red, 0.25 mM sodium pyruvate, 0.3% bovine serum albumin (BSA), 75 μg/ml penicillin G and 25 μg/ml gentamycin sulfate) to collect immature oocytes only. The immature oocytes having cumulus cells closely attached were selected and washed with TL-HEPES-PVA twice, and then washed with the following maturation medium twice. For ex vivo maturation, tissue culture medium (TCM) 199 culture medium (Sigma, St. Louis, Mo., USA) was used as a basic medium, and the culture medium was supplemented with 26.19 mM $NaHCO_3$, 0.2 mM sodium pyruvate, 75 μg/ml sodium penicillin G, and 50 μg/ml streptomycin sulfate. A 4-well plate (NUNC) was added with an ex vivo medium containing 5 μg/ml insulin, 0.5 μg/ml luteinizing hormone (LH), 0.5 μg/ml follicular stimulating hormone (FSH), 10 ng/ml epidermal growth factor (EGF), 0.57 mM cysteine, and 10% porcine follicular fluids (pFF). Then the immature oocytes were transferred thereto and incubated at 38.5° C. in a 5% $CO_2$ incubator for 22 hours. Subsequently, the immature oocytes were incubated for additional 22 hours in a maturation medium excluding FSH and LH. The follicular fluids used in the present invention were the ones that were collected from ovaries removed at a slaughterhouse, then filtered and frozen.

Example 5

Somatic Cell Cloning

Oocytes that were matured for 1 to 44 hours were transferred to the TL-HEPES-PVA supplemented with 0.1% hyaluronidase and the expanded cumulus cells were removed by pipetting. Porcine oocytes were enucleated by micromanipulation under an inverted microscope (Nikon, Japan) which is equipped with a micromanipulator (Narishige, Japan). Then, the porcine fibroblast, which is a donor cell transformed with the sTNFR1-Fc fusion gene prepared in Example 3, was injected into the oocytes. For the fusion of different cells, an electric stimulation of 1.5 kV/cm and 1 DC pulse for 60 μs was applied by an ECM 2001 electrocell manipulator (BTX Inc., San Diego, Calif., USA). The fused oocytes were cultured in a TCM-199 medium for 3 hours, and then transferred to a PZM-3 medium, cultured, and used for embryo transplantation.

Example 6

Aspiration of Embryos

Aspiration of embryos was performed in a laboratory at a room temperature (25 to 35° C.). A petri dish is filled with a medium for embryo transplantation, and the embryos prepared in Example 5 were added thereto. A sterilized 0.2 ml straw was used for cell cryopreservation. It is recommended to use a commercially available straw that is sterilized with gamma ray, but if needed, a straw may be directly sterilized by ethylene oxide (EO) gas.

Aspiration of embryos was performed in the order of media layer-air layer-media layer-air layer-embryo layer-air layer-media layer-air layer-media layer. In this process, it was essential to keep the straw sterilized. If the EO gas-sterilized straw was used, before the aspiration of embryos, the interior of straw was washed by repeating the process of aspirating and discharging the transplantation medium 1 to 3 times. After finishing aspiration, the open side of straw was sealed by using a plastic cap. To keep the aspirated and sealed straw sterile, it was put into the plastic pipette (Falcon, 2 ml), which was cut in a slightly bigger size than the straw, and sealed with a paraffin film. An optimal temperature in the sealed straw was maintained by using a portable incubator, before usage.

Example 7

Production of Transgenic Pig by Transplantation of Embryos

Surrogate mothers which are estrus-synchronized to embryos, were prepared. Embryo transplantation was done by exposing ovary through laparotomy. After anesthetization of surrogate mother, the mid-line of the abdominal region was incised to expose the uterus, ovary, oviduct, and fimbriae. The inlet of oviduct on the side of uterus was found inside the fimbriae. The straw aspirated with embryos was aseptically taken from the portable incubator, and inserted into the inlet of oviduct. The inserted straw was then moved up to the ampullary-isthmic junction region. In this process, the operation was performed rapidly in order to minimize the temperature change of straw, while maintaining the straw at warm temperature with the body temperature of the operator and the exposed uterus. After finishing the insertion, the air-containing layer on the opposite side of straw was cut by scissors. A 1 cc syringe was mounted on the cut end, and approximately 0.3 cc air was injected to release the embryos and medium from the straw into the oviduct. At this time, the top end of 0.2 ml yellow tip was cut by 5 mm and used for connecting the syringe and straw.

Figure 3:
FIG. 3 shows the appearance of transgenic pig that is introduced with a gene encoding sTNFR1-Fc.

After finishing the transplantation of embryos, the exposed uterus, ovary, oviduct, and fimbriae were put back in abdominal cavity, and the abdominal fascia was closed using an absorbable suture material. The surgical site was disinfected with Betadine, and treated with antibiotics and anti-inflammatory analgesic drugs. A pregnancy test was performed for the surrogate mother transplanted with embryos. For the ones confirmed to be pregnant was induced for labor, and a transgenic pig introduced with sTNFR1-Fc was produced (FIG. 3).

Example 8

Confirmation of sTNFR1-Fc Gene Expression in a Transgenic Pig

In order to examine the expression of sTNFR1-Fc gene in a transgenic pig, the tail and ear tissues and blood sample were collected from a newborn transgenic pig.

Genomic DNA was isolated from the obtained tail tissue by using a genomic DNA extraction kit (G-spin™ Genomic DNA Extraction Kit, iNtRON Biotechnology, Korea). Also, RNA was extracted from the blood sample by using a RNA extraction kit (RNeasy Mini kit, Qiagen, Germany) and cDNA was synthesized by reverse-transcriptase PCR. Having the isolated genomic DNA and cDNA as a template, PCR was performed using the sTNFR1-Fc gene-specific primers and Maxime™ PCR premix kit to determine the successful insertion of target gene in the genomic DNA and the mRNA expression. PCR was performed with the step of denaturation at 95° C. for 5 minutes, 30 cycles of denaturation at 95° C. for 30 seconds, annealing at 58° C. for 30 seconds, elongation at 72° C. for 1 minute, and final elongation at 72° C. for 10 minutes.

Figure 4:
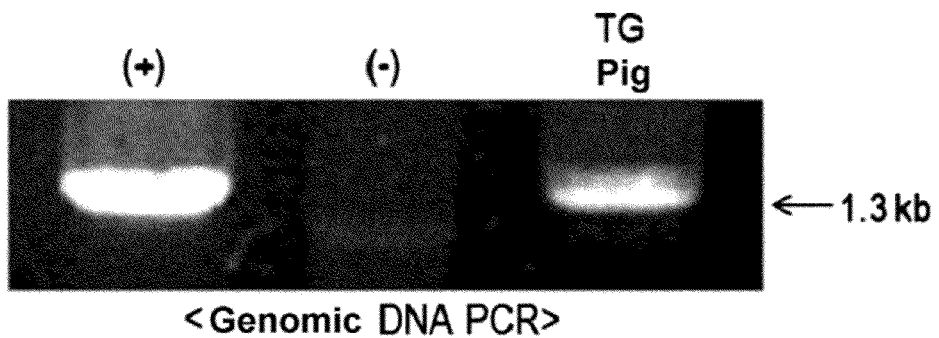
FIG. 4 shows the expression of sTNFR1-Fc fusion protein in the tail tissue and monocytes of peripheral blood of newborn transgenic pig. The first diagram shows the PCR analysis result on the genomic DNA isolated from the tail tissue of newborn transgenic pig, and the second diagram shows the RT-PCR results on monocytes of peripheral blood from the transgenic pig.
Figure 4:
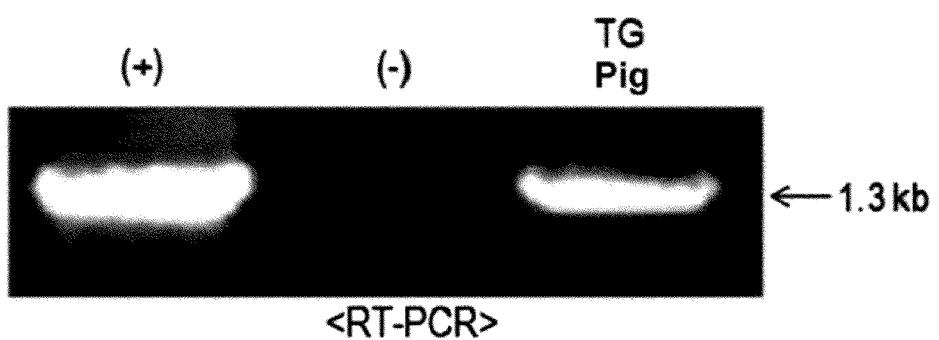

As a result, as shown in FIG. 4, the expression of sTNFR1-Fc gene was observed in the tail tissue and monocytes of peripheral blood of newborn transgenic pig, thereby confirming the generation of desired transgenic pig.

Figure 5:
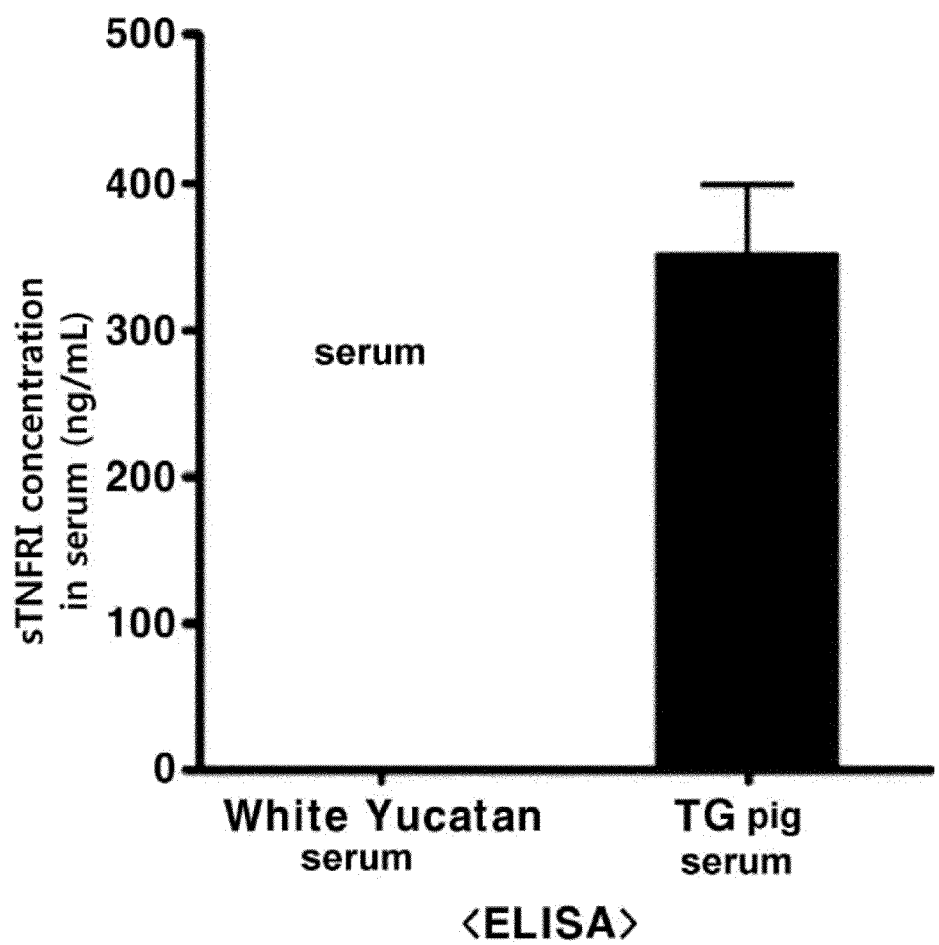
FIG. 5 shows the analysis of the concentration of sTNFR1 in the serum of isolated blood by using the human sTNFR1-specific ELISA kit (R&D system, USA). Also, the expression of human sTNFR1 was observed in the serum of transgenic pig of the present invention.

Also, serum was separated from the isolated blood and the concentration of sTNFR1 in serum was examined by using a human sTNFR1-specific ELISA kit (R&D system, USA). As a result, as shown in FIG. 5, there was no expression of human sTNFR1 in the serum of white yucatan pig, which was a negative control group, whereas the expression of human sTNFR1 was observed in the serum of transformant pig.

Figure 6:
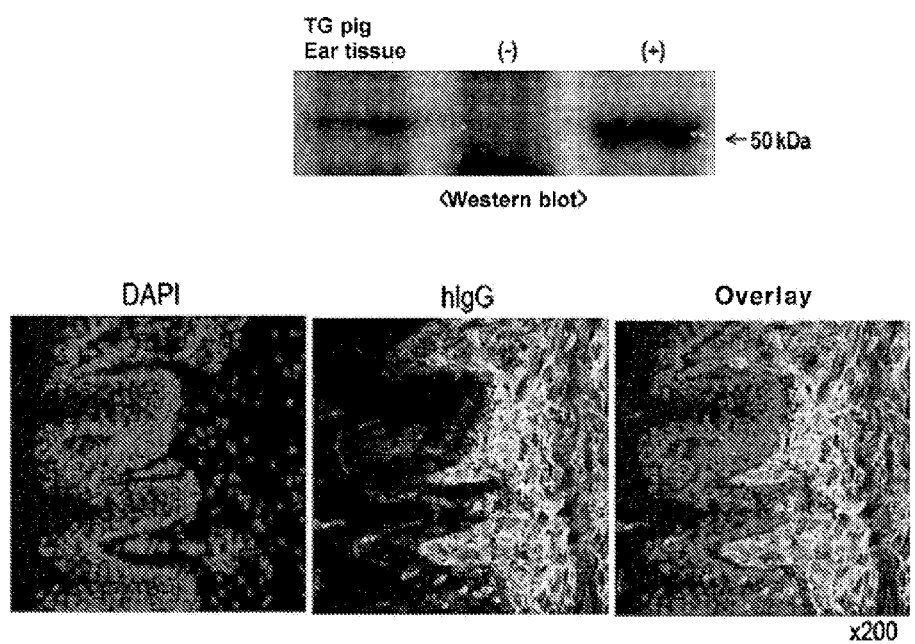
FIG. 6 shows the confirmation of the protein expression of sTNFR1-Fc in the ear tissue removed from the transgenic pig of the present invention through western blotting and immunostaining.

Furthermore, the protein expression of sTNFR1-Fc was examined by western blotting and immunostaining using the obtained ear tissue (FIG. 6). For western blotting, the ear tissue was homogenized and the proteins thereof were separated through electrophoresis. The separated proteins were then transferred to a PVDF membrane. Then the PVDF membrane was blocked with a blocking buffer (5% skim milk in TBST) for 1 hour. After blocking, the membrane was reacted with HRP-conjugated anti-human IgG antibody (Santa Cruz Biotechnology, CA, USA), which was diluted at a ratio of 1:5000, and incubated at a room temperature for 1 hour. After the reaction, the membrane was washed with TBST buffer three times, treated with chemiluminescent substrate and exposed to the film for image development. To perform immunostaining, the ear tissue was fixed with 4% paraformaldehyde and continuously sliced to a thickness of 10 μm using Leica CM1900 Cryostat (Leica microsystem, Germany). Then the sliced fragments were washed with PBS three times, and blocked with blocking buffer (5% normal goat serum) for 30 minutes. After blocking, the tissue fragments were reacted with FITC-conjugated anti-human IgG antibody (ICN Pharmaceuticals, USA), which was diluted at a ratio of 1:360, and incubated at a room temperature for 1 hour. After the reaction, the protein expression was confirmed by using Zeiss LSM 510 Metaconfocal microscope equipped with 488 nm Argon ion laser (Zeiss, Germany).

Through western blotting and immunostaining, it was confirmed that sTNFR1-Fc protein was being expressed in the ear tissue of transformant pig, as shown in FIG. 6.

Example 9

Evaluation of the Function of Transformant Pig

In order to evaluate the function of transformant pig, blood sample was separated from the transformant pig and used for evaluation. The serum was isolated from the obtained blood. Then the evaluation of function was performed by treating the vascular endothelial cell line of pig (MPN3) with the serum or human TNF-α and examining the activation level of the vascular endothelial cell line. The activation level of the vascular endothelial cell line was examined by monitoring the mRNA expression of chemokine through reverse-transcriptase PCR. This was based on the fact that when the vascular endothelial cell of pig is stimulated by human TNF-α, it becomes activated, thereby increasing the expression of chemokine. Each of the 10% wild-type serum and the transformant pig serum was mixed with 20 ng/ml human TNF-α, and then added to the vascular endothelial cell line along with culture medium. After 3 and 6 hours of treatment, the cells were collected and RNA was extracted therefrom using a RNA extraction kit (RNeasy Mini kit, Qiagen, Germany). Subsequently, 1 μg of total RNA of each test group was used to synthesize cDNA by using reverse-transcriptase PCR. Then, PCR was performed to determine the expression of mRNA, using the synthesized cDNA as a template, the primers specific to IP-10 and RANTES among the chemokines of pig, and Maxime™ PCR premix kit. The PCR was performed with a denaturation step at 95° C. for 5 minutes; 30 cycles of a denaturation step at 95° C. for 30 seconds, an annealing step at 62° C. for 30 seconds, and an elongation step at 72° C. for 1 minute; and a final elongation step at 72° C. for 10 minutes.

As a result, as shown in FIG. 7, in the test group that was not added with the serum and the group treated with the wild-type serum, the expressions of IP-10 and RANTES were increased after 3 hours of treatment, however in the group treated with the serum of transformant pig, the expression of chemokine was suppressed. These results suggest that the sTNFR1-Fc protein present in the blood of transformant pig can function as a TNF-α inhibitor.

INDUSTRIAL APPLICABILITY

The transformant pig of the present invention expresses and secretes sTNFR1-Fc not only in the organ or tissue, but also in blood, and thus if the organ separated from the pig is transplanted to the same or different species, it can alleviate the immunorejection and inflammatory response. Therefore, the transformant pig of the present invention can be effectively used as a pig for secreting sTNFR1-Fc or for providing organs.

The invention claimed is:

1. A transgenic pig whose genome comprises the nucleotide sequence of SEQ ID NO:5 encoding a fusion protein of the extracellular domain of human soluble tumor necrosis factor receptor and a human immunoglobulin Fc region (sTNFRI-Fc), wherein organs isolated from the transgenic pig exhibit decreased rejection as compared to a pig not expressing sTNFRI.

2. The transgenic pig according to claim 1, wherein the sTNFRI-Fc inhibits the activity of TNFα.

3. A method for preparing the transgenic pig of claim 1 comprising
   (a) introducing a nucleotide sequence encoding a fusion protein of the extracellular domain of human soluble tumor necrosis factor receptor and a human immunoglobulin Fc region (sTNFRI-Fc) into a somatic cell isolated from a pig to produce an introduced pig somatic cell whose genome comprises the nucleotide sequence;
   (b) fusing the nucleus of the introduced somatic cell into an enucleated porcine oocyte to produce to produce a pig embryo;
   (c) implanting the embryo into a foster mother pig; and
   (d) permitting term birth of the transgenic pig
wherein sTNFRI-Fc is secreted into the blood of the transgenic pig, and wherein organs isolated from the transgenic pig exhibit decreased rejection as compared to a pig not expressing sTNFRI.

4. The method according to claim 3, wherein the pig of step (a) has a blood type O.

5. An organ isolated from the transgenic pig according to claim 1, wherein the organ is comprised of a cell whose genome comprises the nucleotide sequence of SEQ ID NO:5 encoding sTNFRI-Fc, wherein the cells of the organ express sTNFRI and exhibit decreased rejection as compared to a pig not expressing sTNFRI.

6. The organ according to claim 5, comprising blood of the pig, wherein the blood comprises TNFRI-Fc.

7. The organ according to claim 5, which is a heart, stomach, small intestine, large intestine, kidney, liver, lung, pancreas, or islet cells isolated from pancreas.

8. The organ according to claim 5, which exhibits a reduced inflammatory response upon transplantation into a recipient compared to an organ isolated from a pig that does not secrete sTNFRI-Fc into its blood.

9. A somatic porcine donor cell line, the cells of which contain a genome comprising the nucleotide sequence of SEQ ID NO:5 encoding sTNFRI-Fc, and the cells express sTNFRI-Fc.

10. The somatic donor cell line according to claim 9, which is a primary fibroblast cell line isolated from a pig having a blood type O.

11. The somatic donor cell line according to claim 9, wherein the somatic donor cell line has Accession No: KCLRF-BP-00249.

12. A method for obtaining a blood sample, comprising preparing a transgenic pig whose genome comprises the nucleotide sequence of SEQ ID NO:5 encoding sTNFRI-Fc, wherein the sTNFRI-Fc is secreted into the blood of the transgenic pig, and isolating the blood sample.

13. A method for preparing human sTNFRI-Fc, comprising preparing a transgenic pig whose genome comprises the nucleotide sequence of SEQ ID NO:5 encoding sTNFRI-Fc, wherein sTNFRI-Fc is secreted into the blood of the pig, and isolating human sTNFRI-Fc from the blood of the transgenic pig.

14. The method according to claim 13, wherein the isolated human sTNFRI-Fc alleviates inflammatory diseases.

15. The transgenic pig according to claim 1, wherein sTNFRI-Fc is expressed in the tail, ear tissue, or blood of the transgenic pig.

* * * * *